United States Patent
Kujundžič et al.

[11] Patent Number: 6,071,886
[45] Date of Patent: Jun. 6, 2000

[54] β,β-DISTRIBUTED DERIVATIVES OF 9-DEOXO-9A-N-ETHENYL-9A-AZA-9A-HOMOERYTHROMYCIN A

[75] Inventors: Nedjeljko Kujundžič ; Dina Pavlović ; Gabrijela Kobrehel; Gorjana Lazarevski; Željko Kelnerić, all of Zagreb, Croatia

[73] Assignee: Pliva Farmaceutska, Kemijska, Prehrambena I Kozmeticka Industrija, Dionicko Drustvo, Zagreb, Croatia

[21] Appl. No.: 09/223,978

[22] Filed: Dec. 31, 1998

[30] Foreign Application Priority Data

Dec. 31, 1997 [HR] Croatia ................ P970714A

[51] Int. Cl.$^7$ ............ A61K 31/70; C07H 17/08
[52] U.S. Cl. ............ 514/29; 536/7.4; 536/18.5
[58] Field of Search ............ 536/7.2, 7.4, 18.5, 536/29; 514/15, 18.5

[56] References Cited

U.S. PATENT DOCUMENTS 5,629,296  5/1997  Kujundzic et al. ................ 514/29

*Primary Examiner*—Elli Peselev
*Attorney, Agent, or Firm*—Pollock, Vande Sande & Amernick

[57] ABSTRACT

The present invention relates to β,β-disubstituted derivatives of 9-deoxo-9a-N-ethenyl-9a-aza-9a-homoerythromycin A, new semisynthetic antibiotics of macrolide class of the general formula (I)

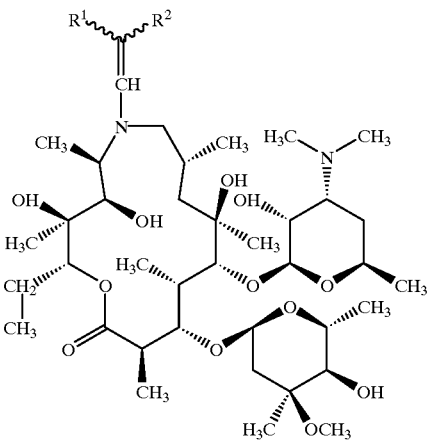

(I)

wherein $R^1$ and $R^2$ are mutually the same or different and represent nitrile, carboxy group of the formula $COOR^3$, wherein $R^3$ represents $C_1$–$C_4$ alkyl group, or keto group of the formula $COR^4$, wherein $R^4$ represents $C_1$–$C_4$ alkyl group, to their pharmaceutically acceptable addition salts with inorganic or organic acids, to a process for the preparation thereof, to a process for the preparation of pharmaceutical compositions, as well as to the use of the obtained pharmaceutical compositions in the treatment of bacterial infections.

21 Claims, No Drawings

β,β-DISTRIBUTED DERIVATIVES OF 9-DEOXO-9A-N-ETHENYL-9A-AZA-9A-HOMOERYTHROMYCIN A

TECHNICAL FIELD

International Patent Classification: A 61 K 31/71, $C_{07}$ H 17/08

TECHNICAL PROBLEM

The present invention relates to β,β-disubstituted derivatives of 9-deoxo-9a-N-ethenyl-9a-aza-9a-homoerythromycin A, new semisynthetic antibiotics of macrolide class with antibacterial action of the general formula (I):

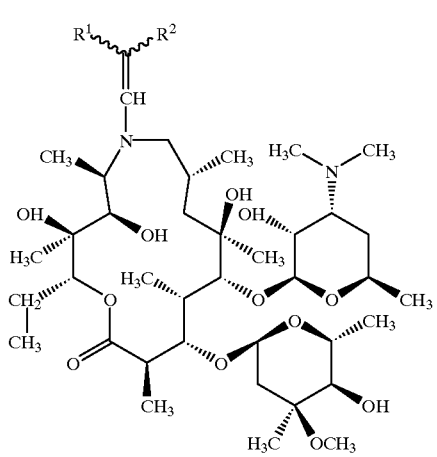

wherein
$R^1$ and $R^2$ are mutually the same or different and represent nitrile, carboxy group of the formula $COOR^3$, wherein $R^3$ represents $C_1$–$C_4$ alkyl group or keto group of the formula $COR^4$, wherein $R^4$ represents $C_1$–$C_4$ alkyl group, to their pharmaceutically acceptable addition salts with inorganic or organic acids, to a process for the preparation thereof, to a process for the preparation of pharmaceutical compositions as well as to the use of the obtained pharmaceutical compositions in the treatment of bacterial infections.

PRIOR ART 9-deoxo-9a-aza-9a-homoerythromycin A is a macrolide antibiotic, whose structure is characterized by a 15-membered macrolactone ring obtained due to the enlargement of a 14-membered ring by incorporation of nitrogen atom. At the same time it is also the first synthetized compound from the new group of semisynthetic macrolides obtained by the incorporation of nitrogen atom into a 14-membered macrolactone ring of azalide.

The antimicrobial activity of the said compound against gram-positive microorganisms is certainly equal to the one of erythromycin A and erythromycin-oxime, whereas it is better than the one of erythromycin A against gram-negative organisms and clinical isolates. The stability in an acidic medium as well as the acute toxicity thereof are more favourable than those of erythromycin-oxime but somewhat worse with respect to erythromycin A.

By reduction of 6,9-imino ether formed by direct Beckmann's rearrangement of 9(E)-oxine with tosyl chloride in a mixture of acetone and water, 9-deoxo-9a-aza-9a-homoerythromycin A is obtained as an intermediate (S. Djokić, G. Kobrehel, G. Lazarevski, N. Lopotar, Z. Tambura šev, B. Kamenar, A. Nagl and I. Vickovič, J. Chem. Soc. Perkin Trans I, 1881, 1986).

In order to obtain compounds having even better biological properties, a great number of new compounds based on 9-deoxo-9a-aza-9a-homoerythromycin A as the starting compound have been prepared.

Acyl derivatives were prepared by selective acylation of 9-deoxo-9a-aza-9a-homoerythromycin A with carboxylic acid anhydrides (S. Djokić, G. Kobrehel and G. Lazarevski, J. Antibiotics, 40, 1006, 1987). By varying both the temperature and the time of the reaction, selectivity of the acylation was achieved. Thus, by the reaction of starting compound at room temperature mono-, di- and triacetyl derivatives were formed. The diacetyl derivative was isolated by the reaction of the starting compound with acetic acid anhydride in pyridine, whereas the monoacetyl derivative was obtained by methanolysis of the starting compound, whereat the 2'—O—acetyl group was removed. By extending the reaction time triacetyl derivative was formed. Tetraacetyl derivative was formed by acetylation of 9-deoxo-9a-aza-9a-homoerythromycin A at increased temperature (70° C.).

In addition to these compounds also 9a-N-formyl-, 9a-N-propionyl-, 2'-O,9a-N-dipropionyl- and 2'-O,9a-N-diformyl-derivatives of 9-deoxo-9a-aza-9a-homoerythromycin A were prepared.

O-Methyl cyclic carbamates were obtained by methylation of triply protected (3',9a)-di-N-2'—O—tris-(benzylchloroformate) followed by deprotection via elimination of the protecting groups in 2'- and 3'-positions (G. Kobrehel, G. Lazarevski, Ž. Kelnerić and S. Djokić, J. Antibiot., 46, 1239, 1993) and the final product was prepared by introducing a methyl group into 3'-position via reductive methylation of the corresponding 3'-des-N-methyl derivatives.

11,12-Cyclic carbonate was obtained by transesterification od 9-deoxo-9a-aza-9a-homoerythromycin A with ethylene carbonate in ethylene acetate (S. Djokić, G. Kobrehel and G. Lazarevski, J Antibiotics, 40, 1006, 1987). In testing on a series of clinical isolates the obtained cyclic carbonate showed better in vitro activity against gram-negative bacteria than erythromycin A.

By reductive methylation of nitrogen in 9a-position of 9-deoxo-9a-aza-9a-homoerythromycin A according to Eschweiler-Clark process, 9-deoxo-9a-methyl-9a-aza-9a-homoerythromycin A—azithromycin—was prepared (S. Djokić and G. Kobrehel, BE 892 357, 1982), which distinguishes itself by its stability in an acidic medium, significantly intensified penetration of tissues and prolonged biological half-life, and posesses also considerable antibacterial a ction against gram-positive and gram-negative bacteria and intracellular pathogenic microorganisms (G. M. Bright A. A. Nagel, J. Bordner, K. A. Desai, J. N. Dibrino, J. Nowakowska, L. Vincent, R. M. Watrous, F. C. Sciavolino, A. R. English, J. A. Retsema, M. R. Anderson, L. A. Brenana, R. J. Borovov, C. R. Cimochowski, J. A. Faiella, A. E. Girard, D. Girard, C. Herbert, M. Manousos and R. Mason, J. Antibiot., 41, 1029, 1988).

According to the known and established prior art β,β-disubstituted derivatives of 9-deoxo-9a-N-ethenyl-9a-aza-9a-homoerythromycin A and their pharmaceutically acceptable addition salts with inorganic or organic acids, a process for the preparation thereof and methods for the preparation of pharmaceutical preparations and the use thereof have hitherto not been described. We have found—which represents an object of the present invention—that β,β-disubstituted derivatives of 9-deoxo-9a-N-ethenyl-9a-aza-9a-homoerythromycin A and their pharmaceutically acceptable addition salts with inorganic or organic acids can be prepared by the reaction of 9-deoxo-9a-aza-9a-homoerythromycin A with substituted ethoxymethylene derivatives and, if appropriate, by the reaction of the obtained β,β-disubstituted derivatives of 9-deoxo-9a-N-ethenyl-9a-aza-9a-homoerythromycin A with inorganic or organic acids, respectively.

TECHNICAL SOLUTION

It has been found that β,β-disubstituted derivatives of 9-deoxo-9a-N-ethenyl-9a-aza-9a-homoerythromycin A of the general formula (I)

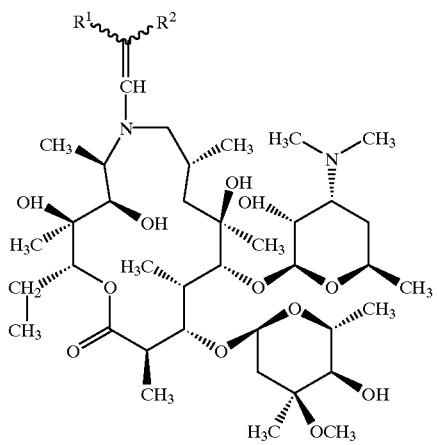

(I)

wherein
$R^1$ and $R^2$ are mutually the same or different and represent nitrile, carboxy group of the formula $COOR^3$, wherein $R^3$ represents $C_1$–$C_4$ alkyl group, or keto group of the formula $COR^4$, wherein $R^4$ represents $C_1$–$C_4$ alkyl group, and their pharmaceutically acceptable addition salts with inorganic or organic acids can be prepared by the reaction of 9-deoxo-9a-aza-9a-homoerythromycin A of the formula (II)

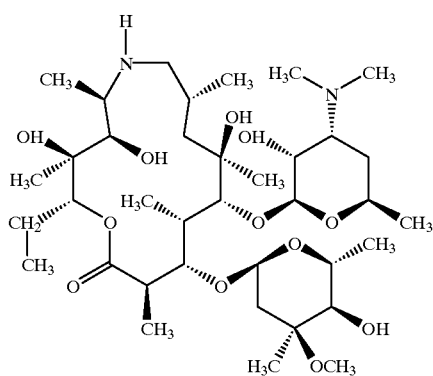

(II)

with ethoxymethylene derivatives of the general formula (III)

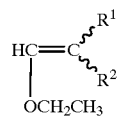

(III)

wherein
$R^1$ and $R^2$ are mutually the same or different and represent nitrile, carboxy group of the formula $COOR^3$, wherein $R^3$ represents $C_1$–$C_4$ alkyl group, or keto group of the formula $COR^4$, wherein $R^4$ represents $C_1$–$C_4$ alkyl group. The reaction is performed in toluene, xylene or some other aprotic solvent at a temperature of 20–115° C.

Pharmaceutically acceptable addition salts representing another object of the present .—. invention are obtained by the reaction of β,β-disubstituted derivatives of 9-deoxo-9a-N-ethenyl-9a-aza-9a-homoerythromycin A with an equimolar amount of a suitable inorganic or organic acid such as hydrochloric, hydroiodic, sulfuric, phosphoric, acetic, trifluoroacetic, propionic, benzoic, benzenesulfonic, methanesulfonic, laurylsulfonic, stearic, palmitic, succinic, ethylsuccinic, lactobionic, oxalic, salicylic acids and the like in a solvent inert to the reaction.

β,β-Disubstituted derivatives of 9-deoxo-9a-N-ethenyl-9a-aza-9a-homoerythromycin A of the general formula (I) and their pharmaceutically acceptable addition salts with inorganic and organic acids posses antibacterial in vitro activity similar to the one of erythromycin. Thus, they can be used for the same purpose and to the same manner as erythromycin A. Their activity is determined by the method of dilution on microplates according to the protocol of National Committee for Clinical Laboratory Standards (NCCLS, M7-A2). The obtained results expressed as minimal inhibitory concentrations (MIC in mcg/ml) indicate their potential use as agents for sterilizing e.g. rooms and medicinal instruments and as industrial antimicrobial agents e.g. for the protection of wood and wall coatings.

The process for the preparation of β,β-disubstituted derivatives of 9-deoxo-9a-N-ethenyl-9a-aza-9a-homoerythromycin A is illustrated by the following Examples, which do not limit the scope of the invention in any way.

EXAMPLE 1

9-Deoxo-9a-N-(β,β-dicarbethoxyethenyl)-9a-aza-9a-homoerythromycin A

A mixture of 9-deoxo-9a-aza-9a-homoerythromycin A (7.27 g, 0.01 mole) and diethyl ethoxymethylene malonate (10.36, 0.04 mole) was heated for 12 hours at a temperature of 100–105° C. Then it was cooled and passed over a silica gel column under eluation first with chloroform and subsequently with a mixture of solvents $CHCl_3$:MeOH=9:1. Pure 9-deoxo-9a-N-(β,β-dicarbethoxyethenyl)-9a-aza-9a-homoerythromycin A was obtained. An analysis of the spectroscopic method spectra (NMR, IR and MS) indicated the anticipated and expected structure of the compound.

EXAMPLE 2

9-Deoxo-9a-N-(β-cyano-β-carbethoxyethenyl)-9a-aza-9a-homoerythromycin A

A solution of 9-deoxo-9a-aza-9a-homoerythromycin A (7.27 g, 0.01 mole) and ethyl ethoxymethylene cyanoacetate (2.0 g, 0.018 mole) in toluene (50.0 ml) was stirred for 18 hours at a temperature of 110–115° C. After cooling the reaction mixture to room temperature a resinous precipitate separated. The toluene solution was decanted and the resinous precipitate was first dissolved in acetone (15.0 ml), whereafter the solution was evaporated to dryness. A crude product (3.27 g) was obtained, wherefrom by chromatography on a silica gel column in the solvent system CHCl$_3$:MeOH=9:1 9-deoxo-9a-N-(β-cyano-β-carbethoxyethenyl)-9a-aza-9a-homo-erythromycin A was obtained. An analysis of the spectroscopic method spectra (NMR, IR and MS) indicated the anticipated and expected structure of the compound.

EXAMPLE 3

9-Deoxo-9a-N-(β,β-dicyanoethenyl)-9a-aza-9a-homoerythromycin A

A solution of 9-deoxo-9a-aza-9a-homoerythromycin A (7.27 g, 0.01 mole) and (ethoxy-methylene)-malonic dinitrile (1.6 g, 0.01 mole) in toluene (30.0 ml) was stirred for about 8 hours at a temperature about 70° C. After cooling the reaction mixture to the room temperature a resinous precipitate separated. The toluene solution was decanted and the resin precipitate was first dissolved in acetone (15.0 ml), whereafter the solution was evaporated to dryness. A crude product (3.31 g) was obtained, wherefrom by chromatography on a silica gel column in the solvent system CHCl$_3$:MeOH=9:3 9-deoxo-9a-N-(β,β-dicyanoethenyl)-9a-aza-9a-homoerythromycin A was obtained. An analysis of the spectroscopic method spectra (NMR, IR and MS) indicated the anticipated and expected structure of the compound.

EXAMPLE 4

9-Deoxo-9a-N-(β-acetyl-β-carbethoxyethenyl)-9a-aza-9a-homoerythromycin A

A solution of 9-deoxo-9a-aza-9a-homoerythromycin A (7.27 g, 0.01 mole) and ethyl-α-(ethoxymethylene)-acetoacetate (2.0 ml, 0.011 mole) in toluene (30.0 ml) was stirred about 6 hours at a temperature of 110–115° C. After cooling the reaction mixture to room temperature a resinous precipitate separated. The toluene solution was evaporated at reduced pressure (2,13×10$^3$ Pa ). A crude product (4.84 g) was obtained, wherefrom by chromatography on a silica gel column in the solvent system CHCl$_3$:MeOH=9: 1 9-deoxo-9a-N-(β-acetyl-β-carbethoxyethenyl)-9a-aza-9a-homoerythromycin A was obtained. An analysis of the spectroscopic method spectra (NMR, IR and MS) indicated the anticipated and expected structure of the compound.

What is claimed is:

1. A β,β-disubstituted derivative of 9-deoxo-9a-N-ethenyl-9a-aza-9a-homoerythromycin A of the formula (I)

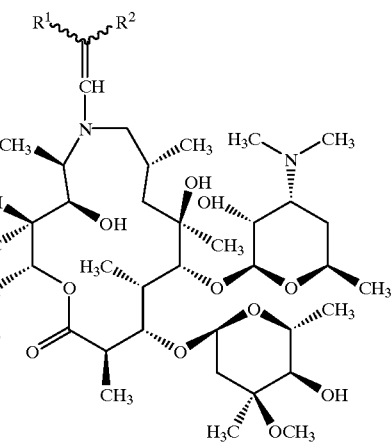

wherein
   $R^1$ and $R^2$ are the same or different and represent nitrile, carboxy group of the formula COOR$^3$, wherein R$^3$ represents C$_1$–C$_4$ alkyl group, or keto group of the formula COR$^4$, wherein R$^4$ represents C$_1$–C$_4$ alkyl group, or its pharmaceutically acceptable addition salt with an inorganic or organic acid.

2. A derivative or its pharmaceutically acceptable salt according to claim 1, characterized in that R$^1$ and R$^2$ are the same and represent carboxy group of the formula COOR$^3$.

3. A derivative or its pharmaceutically acceptable salt according to claim 2, characterized in that R$^3$ represents C$_1$–C$_4$ alkyl group.

4. A derivative or its pharmaceutically acceptable salt according to claim 3, characterized in that C$_1$–C$_4$ alkyl group represents ethyl group.

5. A derivative or its pharmaceutically acceptable salt according to claim 1, characterized in that one of R$^{1\ and\ R2}$ represents nitrile and the other of R$^1$ and R$^2$ represents carboxy group of the formula COOR$^3$.

6. A derivative or its pharmaceutically acceptable salt according to claim 5, characterized in that R$^3$ represents C$_1$–C$_4$ alkyl group.

7. A derivative or its pharmaceutically acceptable salt according to claim 6, characterized in that C$_1$–C$_4$ alkyl group represents ethyl group.

8. A derivative or its pharmaceutically acceptable salt according to claim 1, characterized in that R$^1$ and R$^2$ are the same and represent nitrile.

9. A derivative or its pharmaceutically acceptable salt according to claim 1, characterized in that one of R$^1$ and R$^2$ represents carboxy group of the formula COOR$^3$ and the other of R$^1$ and R$^2$ represents keto group of the formula COR$^4$.

10. A derivative or its pharmaceutically acceptable salt according to claim 9, characterized in that R$^3$ represents C$_1$–C$_4$ alkyl group.

11. A derivative or its pharmaceutically acceptable salt according to claim 10, characterized in that C$_1$–C$_4$ alkyl group represents ethyl group.

12. A derivative or its pharmaceutically acceptable salt according to claim 9, characterized in that R$^4$ represents C$_1$–C$_4$ alkyl group.

13. A derivative or its pharmaceutically acceptable salt according to claim 12, characterized in that C$_1$–C$_4$ alkyl group represents methyl group.

14. A process for the preparation of a β,β-disubstituted derivative of 9-deoxy-9a-N-ethenyl-9a-aza-9a- homoerythromycin A of the formula (I)

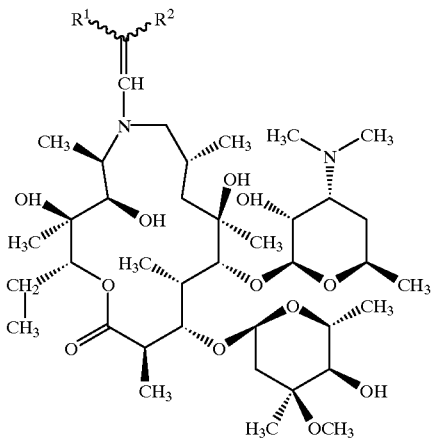

wherein
R¹ and R² are the same or different and represent nitrile or carboxy group of the formula $COOR^3$, wherein $R^3$ represents $C_1$–$C_4$ alkyl group, or keto group of the formula $COR^4$, wherein $R^4$ represents $C_1$–$C_4$ alkyl group, or its pharmaceutically acceptable addition salt with an inorganic or organic acid, characterized in that 9-deoxo-9a-aza-9a-homoerythromycin A of the formula (II)

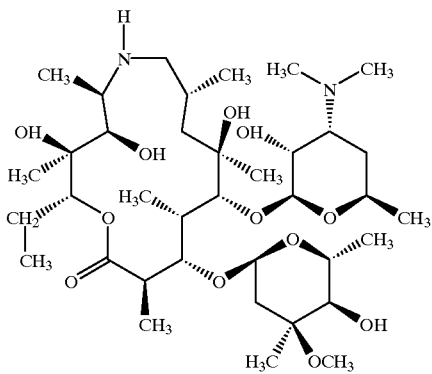

is subjected to a reaction with ethoxymethylene derivatives of the general formula (III)

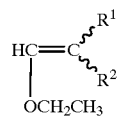

wherein
R¹ and R² are the same or different and represent nitrile, carboxy group of the formula $COOR^3$, wherein $R^3$ represents $C_1$–$C_4$ alkyl group, or keto group of the formula $COR^4$, wherein $R^4$ represents $C_1$–$C_4$ alkyl group, whereat the reaction is performed in an aprotic solvent at a temperature of 20–115° C., and then, it appropriate, to a reaction with an inorganic or organic acid.

15. The process according to claim 14 wherein the aprotic solvent comprises toluene or xylene.

16. Pharmaceutical composition comprising a pharmaceutically acceptable carrier and an antibacterially effective amount of a derivative or its pharmaceutically acceptable salt according to claim 1.

17. A method for treating bacterial infection which comprises administering to a patient in need thereof an effective amount for treating the bacterial invention of a derivative or its pharmaceutically acceptable salt according to claim 1.

18. A method for treating bacterial infection which comprises administering to a patient in need thereof an effective amount for treating the bacterial invention of a derivative or its pharmaceutically acceptable salt according to claim 1.

19. A method for treating bacterial infection which comprises administering to a patient in need thereof an effective amount for treating the bacterial invention of a derivative or its pharmaceutically acceptable salt according to claim 1.

20. A method for treating bacterial infection which comprises administering to a patient in need thereof an effective amount for treating the bacterial invention of a derivative or its pharmaceutically acceptable salt according to claim 4.

21. A method for treating bacterial infection which comprises administering to a patient in need thereof an effective amount for treating the bacterial invention of a derivative or its pharmaceutically acceptable salt according to claim 5.

* * * * *